(12) United States Patent
Garvey et al.

(10) Patent No.: US 11,452,538 B2
(45) Date of Patent: Sep. 27, 2022

(54) SURGICAL DEVICE INCLUDING A CANNULA HAVING A COMBINATION TRACK

(71) Applicant: Mission Surgical Innovations, LLC, Media, PA (US)

(72) Inventors: Brian Garvey, Media, PA (US); Sidney M. Jacoby, Gladwyne, PA (US); Patrick Kane, Ocean City, NJ (US); Eon Kyu Shin, Princeton, NJ (US); Garvey Jonassaint, Chester Springs, PA (US)

(73) Assignee: MISSION SURGICAL INNOVATIONS, LLC, Media, PA (US)

( * ) Notice: Subject to any disclaimer, the term of this patent is extended or adjusted under 35 U.S.C. 154(b) by 17 days.

(21) Appl. No.: 15/385,393

(22) Filed: Dec. 20, 2016

(65) Prior Publication Data
US 2017/0252056 A1 Sep. 7, 2017

Related U.S. Application Data

(60) Provisional application No. 62/301,829, filed on Mar. 1, 2016.

(51) Int. Cl.
*A61B 1/00* (2006.01)
*A61B 1/313* (2006.01)
(Continued)

(52) U.S. Cl.
CPC .... *A61B 17/320036* (2013.01); *A61B 1/0014* (2013.01); *A61B 1/00147* (2013.01);
(Continued)

(58) Field of Classification Search
CPC ...... A61B 17/320036; A61B 17/00008; A61B 1/018; A61B 17/320016; A61B 1/00087;
(Continued)

(56) References Cited

U.S. PATENT DOCUMENTS

| 5,273,024 A | 12/1993 | Menon et al. |
| 5,827,312 A | 10/1998 | Brown et al. |

(Continued)

FOREIGN PATENT DOCUMENTS

| WO | 2007145716 A2 | 12/2007 |
| WO | 2015033907 A1 | 3/2015 |

*Primary Examiner* — Alexandra L Newton
(74) *Attorney, Agent, or Firm* — Volpe Koenig (57) ABSTRACT

A surgical device includes a cannula for use in combination with one or more surgical implements. The cannula includes a base member at a proximal end, a sidewall connected to the base member; and a bore defined by the base member and the sidewall. The sidewall further has an opening into the bore between axially-extending edges of the sidewall. The base member includes a combination track including a first section and a second section. The first section is an opening through the base member into the bore and the second section is an opening into an action area outside of the bore and radially between the edges of the sidewall. The combination track is configured to slidably receive a first surgical implement through the first section and into the bore and slidable receive a second surgical implement through the second section and into the action area.

18 Claims, 12 Drawing Sheets

(51) Int. Cl.
*A61B 17/32* (2006.01)
*A61B 17/3209* (2006.01)
*A61B 17/00* (2006.01)

(52) U.S. Cl.
CPC .............. *A61B 17/32* (2013.01); *A61B 1/313* (2013.01); *A61B 17/3209* (2013.01); *A61B 2017/00477* (2013.01); *A61B 2017/320052* (2013.01)

(58) Field of Classification Search
CPC .............. A61B 1/00128; A61B 1/0014; A61B 2017/00778; A61B 2017/320052; A61B 1/00135
See application file for complete search history.

(56) References Cited

U.S. PATENT DOCUMENTS

| | | | |
|---|---|---|---|
| 6,179,852 B1 * | 1/2001 | Strickland | A61B 17/320036 606/167 |
| 6,569,085 B2 | 5/2003 | Kortenback et al. | |
| 7,431,694 B2 | 10/2008 | Stefanchik et al. | |
| 7,780,690 B2 * | 8/2010 | Rehnke | A61B 1/313 600/104 |
| 7,959,561 B2 * | 6/2011 | Akui | A61B 1/00087 600/121 |
| 8,257,379 B2 | 9/2012 | Lee | |
| 8,273,098 B2 | 9/2012 | Strickland | |
| 8,523,891 B2 | 9/2013 | Welborn | |
| 8,523,892 B2 | 9/2013 | Rehnke et al. | |
| 8,672,960 B2 | 3/2014 | Briganti et al. | |
| 2004/0054378 A1 * | 3/2004 | Yang | A61B 17/320036 606/191 |
| 2010/0228085 A1 * | 9/2010 | Mirza | A61B 1/018 600/106 |
| 2012/0016397 A1 * | 1/2012 | Briganti | A61B 17/320036 606/167 |
| 2012/0016398 A1 * | 1/2012 | Strickland | A61B 17/320036 606/170 |
| 2014/0066709 A1 * | 3/2014 | Mirza | A61B 17/32002 600/106 |

\* cited by examiner

SURGICAL DEVICE INCLUDING A CANNULA HAVING A COMBINATION TRACK

PRIORITY CLAIM

This application claims priority under 35 U.S.C. § 119 to U.S. Provisional Application No. 62/301,829, filed on Mar. 1, 2016 which is expressly incorporated by reference herein in its entirety.

FIELD OF INVENTION

The present disclosure relates to a surgical device, and, more particularly, to a surgical device including a cannula having a combination track for slidably receiving more than one surgical implement.

BACKGROUND

Several soft tissue procedures involve the division or release of a soft tissue (ligament, tendon, muscle, fascia, etc.) with a knife blade to decompress adjacent nerves or other soft tissues. Conventional soft tissue surgery is performed either in an open manner with large incisions; in a mini-open manner with a smaller incision, or endoscopically with the assistance of visualization and tissue manipulation through one of several types of guides or apparatuses. Open procedures are more disruptive to the patient and often do not utilize surgical guides to protect the adjacent soft tissue structures. Open and mini-open procedures require the incision to be placed directly over the structure subject to release. Often times the incision in an open or mini-open procedure must be made in an anatomic location that provides additional discomfort to the patient and increased potential for post-operative complications. Endoscopic systems comprise guides that allow the incision placement adjacent to the tissue being released. Surgeons then have more variability in the placement of the incision which provides the patient with a potential for faster recovery and decreased pain or discomfort post-surgery.

Conventional endoscopic systems have several limitations depending on their independent design features. Many conventional endoscopic systems do not allow the blade and endoscope or arthroscope to move independently from each other. These systems require the scope to be mounted to the cannula and blade mechanism which may be static or deployed through a secondary mechanism. The inability to move the scope and blade independently through a guide or cannula limits the physical control and visualization available to the surgeon. The surgeon must move the entire assembly of the scope, guide and knife as one unit, and cannot reposition the camera relative to the knife or guide. This can prevent the surgeon from confirming with 100% certainty that the soft tissue was appropriately manipulated or released. Additionally, the inability to move the blade and scope independently of each other provides the potential for the surgeon to cut adjacent soft tissues, such as nerves, without knowing. Also if the view through the scope becomes obscured via moisture or debris, the surgeon must remove the entire apparatus from the body, disassemble the scope from the guide and blade, remove the obstruction to the view, reassemble and reinsert the apparatus. This practice adds significant time and inconvenience to the surgery.

The present disclosure is directed to overcoming one or more problems of the prior art.

SUMMARY

In one aspect, the present disclosure is directed to a cannula for use as part of a surgical device. The cannula includes a base member at a proximal end, a sidewall connected to the base member and extending in an axial direction from the proximal end to a distal end, and a bore extending in the axial direction defined by the base member and the sidewall, the sidewall further defining an opening into the bore between axially-extending edges of the sidewall. The base member includes a combination track including a first section and a second section. The first section is an opening through the base member into the bore and the second section is an opening into an action area outside of the bore and radially between the edges of the sidewall. The combination track is configured to slidably receive a first surgical implement through the first section and into the bore and slidable receive a second surgical implement through the second section and into the action area.

In another aspect, the present disclosure is directed to a surgical device. The surgical device includes a first surgical implement, a second surgical implement including an acting feature and a sliding feature, and a cannula. The cannula includes a base member at a proximal end, a sidewall connected to the base member and extending in an axial direction from the proximal end to a distal end, and a bore extending in the axial direction defined by the base member and the sidewall. The sidewall defines an opening into the bore between axially-extending edges of the sidewall. The base member includes a combination track including a first section and a second section, the first section being an opening through the base member into the bore and the second section being an opening into an action area outside of the bore and radially between the edges of the sidewall. The combination track slidably receives the first surgical implement through the first section and into the bore and slidably receives the second surgical implement through the second section and into the action area via the sliding feature.

In yet another aspect, the present disclosure is directed to a method of performing a surgical procedure. The method includes inserting a cannula into an incision. The cannula includes a base member defining a combination track, the combination track including a first section being an opening into a bore formed by a sidewall and a second section being an opening into an action area outside of the bore and radially between axially-extending edges of the sidewall. The method further includes inserting a camera device into the bore through the first section of the combination track and sliding the camera device toward a distal end of the cannula, providing an image of a target tissue via the camera device, and inserting a tissue manipulation device into the action area through the second section of the combination track and sliding the tissue manipulation device toward the distal end of the cannula. The method further includes manipulating the target tissue via the tissue manipulation device

BRIEF DESCRIPTION OF THE DRAWING(S)

The foregoing Summary and the following detailed description will be better understood when read in conjunction with the appended drawings, which illustrate a preferred embodiment of the invention. In the drawings.

DETAILED DESCRIPTION OF THE PREFERRED EMBODIMENT(S)

The present disclosure provides a surgical device which is generally applicable to procedures which include the insertion of an instrument through an incision and the manipulation of a selected tissue with the instrument. The disclosed surgical device includes multiple components which are used in conjunction with each other to execute the procedure and which include features which enhance and ease such execution.

The disclosed surgical device includes a cannula which forms a base structure and includes an integral track defined along an axis of the cannula. The track includes at least first and second sections which define axially-extending spaces for receiving other components of the surgical device. For example, the track includes a first portion for receiving a first implement and a second portion for receiving a second implement. The first implement may be a camera device which provides an internal view of a target tissue for a person performing the procedure. The second implement may be a tissue manipulation device which is guided by the person performing the procedure and which may be used to manipulate (e.g., cut) the target tissue.

The disclosed cannula having a combination track provides an improved mechanism for performing a tissue manipulation procedure. The first and second sections of the track, which are interconnected in space, allow the different surgical implements to be positioned in close proximity to each other, providing for effective interaction and use of the implements. For example, with the disclosed combination track a camera device may be positioned directly beneath a tissue manipulation device, providing a clear view for performance of the procedure. Moreover, the combination track allows the surgical implements to interact with each other, such as to allow one implement to provide a guide structure for the other implement.

Figure 1:
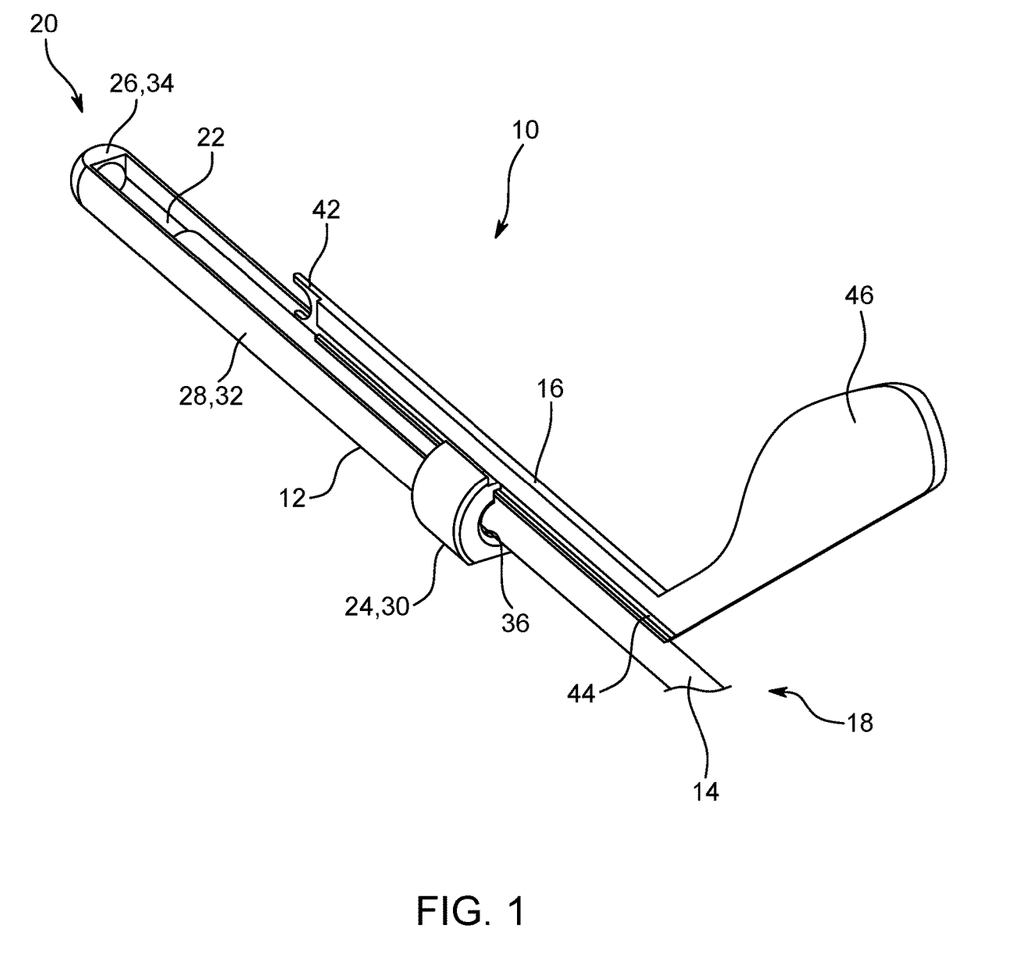
FIG. 1 is a perspective view of an exemplary surgical device including a cannula and surgical implements.
Figure 2:
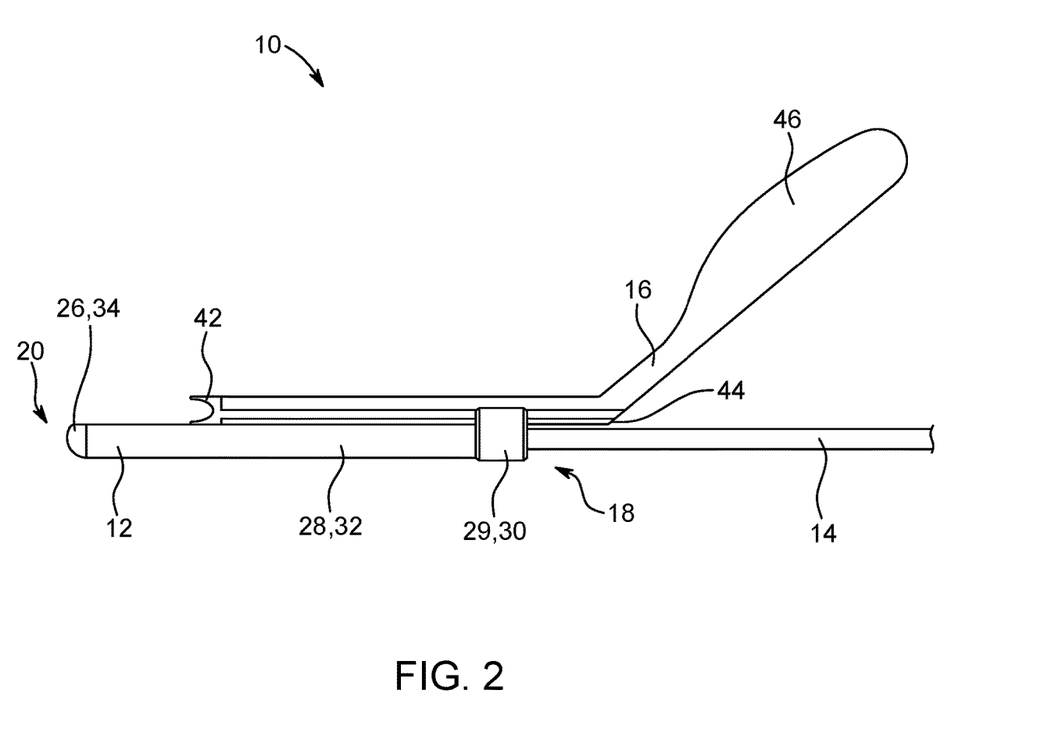
FIG. 2 is a side view of the cannula and implements of FIG. 1.

FIGS. 1-2 illustrate perspective and side views, respectively, of an exemplary surgical device 10. The surgical device 10 is configured to be used in a surgical procedure, such as a tissue manipulation procedure. For example, the surgical device 10 may be configured to be used in a procedure for releasing, excising, or modifying soft tissue structures. Examples of such procedures which may be carried out using the surgical device 10 include carpal tunnel release, cubital tunnel release, trigger finger release, gastrocnemius release, and plantar facia release. These and similar procedures nominally include minimally-invasive techniques which are generally assisted through the use of a device (e.g., a camera) which provides visualization of an internal structure which is being targeted for the procedure. The surgical device 10 includes features which allow for such a visualization device to be used in combination with an implement which is used to carry out the surgical component of the procedure.

Consistent with disclosed embodiments, the surgical device 10 includes a cannula 12, a first surgical implement 14, and a second surgical implement 16. The cannula 12 is a base element which includes a proximal end 18 and a distal end 20 along an axial direction of the cannula 12. As shown in FIG. 1, a bore 22 extends along the axial direction through the cannula 12.

Figure 3:
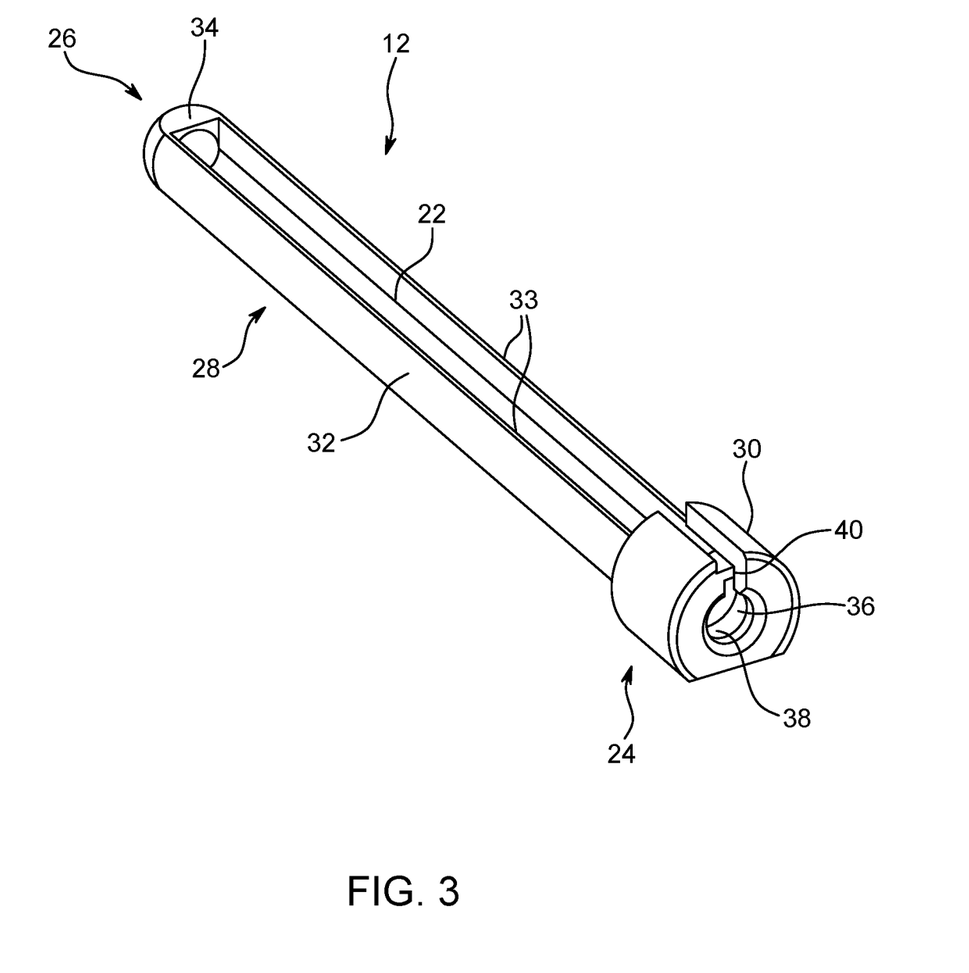
FIG. 3 is a perspective view of the cannula of FIG. 1.

FIG. 3 further illustrates the cannula 12. In an exemplary embodiment, the cannula 12 includes an end portion 24 at the proximal end 18, an end portion 26 at the distal end 20, and a tubular body portion 28 formed therebetween. The bore 22 may extend an entire length of the cannula 12. In a preferred embodiment, the end portion 26 is closed in order to act as a stop for the first surgical implement 14.

In an exemplary embodiment, the end portion 24 of the cannula 12 includes a base member 30 formed as an enlarged portion in comparison to the tubular body portion 28. The tubular body portion 28 includes a sidewall 32 which extends axially and radially and defines the bore 22 therethrough and preferably includes a pair of axially-extending edges 33 which define an opening into the bore 22 (e.g., from above). The end portion 26 may include a support surface 34.

The base member 30 formed at the end portion 24 of the cannula 12 defines a combination track 36 for slidably receiving both the first surgical implement 14 and the second surgical implement 16. As will be described in more detail, the combination track 36 includes a first section 38 which is an opening into the bore 22 and a second section 40 which is a connected opening to an area outside of and adjacent to the bore 22, which may be an area radially between the axially-extending edges 33 of the sidewall 32. As used herein, an area is "radially between" the edges when a corresponding space is between parallel planes which pass through the edges.

In an exemplary embodiment, the area between the edges 33 of the sidewall 32 is also above the opening into the bore 22 when the cannula 12 is inserted into a patent through an incision (i.e., during use). In a particular embodiment, the area between the edges is entirely above the opening into the bore 22. The first section 38 is configured to receive the first surgical implement 14 therein, with the first surgical implement 14 sliding through the associated opening and into the bore 22. The second section 40 is configured to receive the second surgical implement 16 therein, with the second surgical implement 16 sliding through the associated opening to the area between the edges 33 of the just above the bore 22.

The tubular body portion 28 extends axially from the base member 30 to the support surface 34. The sidewall 32 extends radially to form a supporting member for the first surgical implement 14. In the illustrated embodiment, the sidewall extends radially to form a semi-circular shape with an open top area between the axially-extending edges 33 of the sidewall 32. It should be understood however, that the sidewall 32 could be formed in other shapes, including a closed circle, rectangular, hexagonal, etc., and may include openings at radial positions other than or in addition to the top opening. In general, the tubular body portion 28 forms a surface for supporting and guiding the first surgical implement 14 in some manner.

In an exemplary embodiment, the support surface 34 at the end portion 26 of the cannula 12 is an extension of the sidewall 32 such that a closed tubular portion is formed. In some embodiments, the support surface 34 is a flat surface extending in a direction perpendicular to the axial direction. In the illustrated embodiment, the support surface 34 also extends along the axially-extending edges 33 of the sidewall 32 in an axial direction. In use, the distal end 20 of the cannula 12 is inserted first in an incision. The support surface 34 contacts soft tissue structures at the surgical sight, providing support and inhibiting the soft tissue structures from blocking the bore 22, thereby limiting the potential of the soft tissue structures from contacting or impeding the view or motion of the surgical implements 14, 16.

The cannula 12 may be formed from suitable material which is acceptable for being temporarily inserted into the human body during a surgical procedure. For example, the cannula 12 may be formed from a medically-acceptable plastic material. Metal materials are also possible. The cannula 12 may be manufactures using an opaque, translucent, or transparent material.

Returning to FIGS. 1-2, it can be seen that the first surgical implement 14 and the second surgical implement 16 are slidably received in the combination track 36. In an exemplary embodiment, the first surgical implement 14 is a camera device, such as an endoscope or an arthroscope, and the second surgical implement 14 is a tissue manipulation device, such as a rasp, a probe, a hook, a feeler, a reverse or antegrade cutting instrument, a forward cutting instrument, or the like. The first surgical implement 14, as a camera device, preferably includes conventional components (e.g., camera components, electronic components, connector components) which allow an image to be presented to a person performing the procedure (e.g., via a connected display).

The second surgical implement 16 may include various features, including, for example, an acting feature 42, a sliding feature 44, and a handle feature 46. The acting feature 42 is preferably a component (e.g., blade, clamp, hook, etc.) which is capable of completing a surgical task (e.g., cutting, moving, modifying, etc.). The sliding feature 44 preferably includes a structure which interacts with the cannula 12 to allow the second surgical implement 16 to be guided relative to the first surgical implement 14. The handle feature 46 is, for example, an upwardly-extending handle which allows a person to easily grasp and move the second surgical implement 16.

In use, the camera device slides through the first section 38 of the combination track 36, into the bore 22 until it reaches the distal end 20. The camera device thereby supplies a visualization of a target tissue at which the distal end 20 is positioned in a patient. The opening of the bore 22 at the distal end 20 provides an axial line of sight for the camera device while the opening formed by the sidewall 32 provides a radial line of sight. The tissue manipulation device slides through the second section 40 of the combination track 36, adjacent to the camera device. The second section 40 guides the tissue manipulation device such that the surgical procedure may be carried out with assistance from the visualization provided by the camera device.

Figure 4:
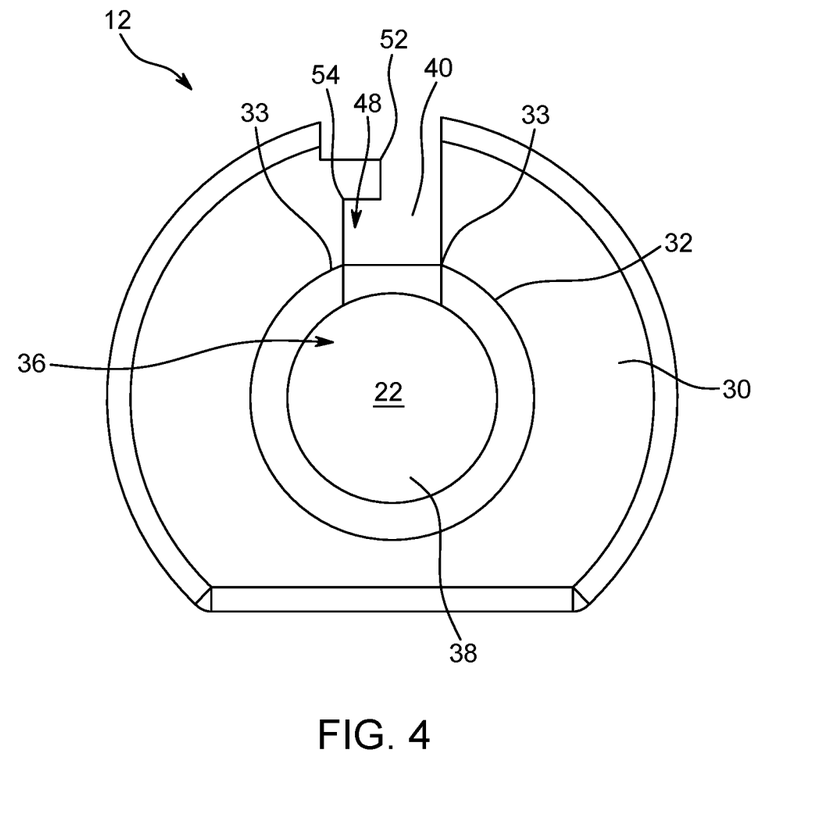
FIG. 4 is an axial view of the cannula of FIG. 1.

FIG. 4 is an axial view of the cannula 12, providing a view in the axial direction. FIG. 4 illustrates an exemplary embodiment of the base member 30 and combination track 36. The combination track 36 includes the first section 38 formed as a circular opening into the bore 22. The combination track 36 further includes the second section 40 formed as an opening into the area adjacent to the bore 22. The opening is thus formed so that the second surgical instrument 16 may be introduced along an axis parallel to the axis of the bore 22.

Figure 5:
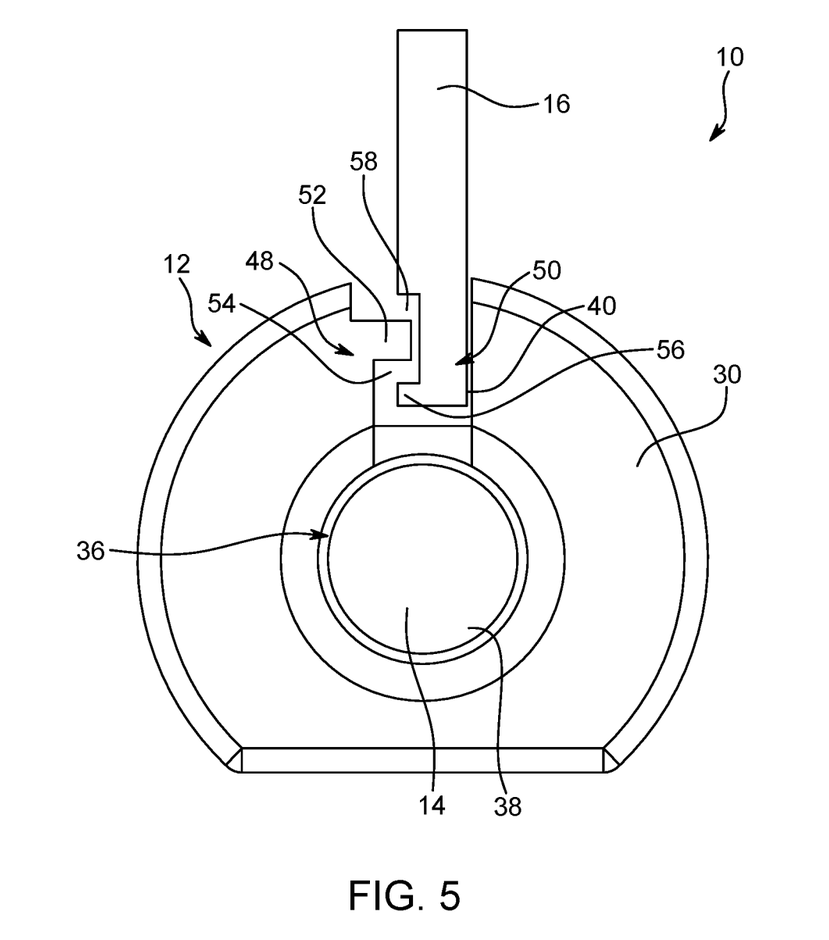
FIG. 5 is an axial view of the cannula and implements of FIG. 1.

In some embodiments, such as in the embodiment of FIG. 4, the combination track 36 includes a mating feature 48. FIG. 5 further illustrates the side axial view of the surgical device 10, including the first and second surgical implements positioned in the cannula 12. As shown, the first surgical implement 14 is positioned via axial insertion into the first section 38 of the combination track 36.

The second surgical implement 16 is positioned above the first surgical implement 14 via the second section 40 of the combination track 36. In the illustrated embodiment, the second surgical implement 16 includes a mating feature 50 formed as part of the sliding feature 44 and which corresponds to the mating feature 48. The corresponding mating features 48, 50 provide a guide structure which helps to control and limit the sliding action of the second surgical implement 16.

In the embodiment of FIGS. 4-5, the mating feature 48 includes a protuberance 52 formed by the base member 30 which creates an groove 54 in the space which makes up the second section 40 of the combination track 36. The mating feature 50 includes an oppositely-disposed protuberance 56 formed by the body of the second surgical implement 16 which creates a corresponding groove 58. As shown in FIG. 5, the protuberance 52 is received in the groove 58 and the protuberance 56 is received in the groove 54 such that the base member 30 and the second surgical implement 16 are interlocked for guided sliding of the second surgical implement 16.

Figure 6:
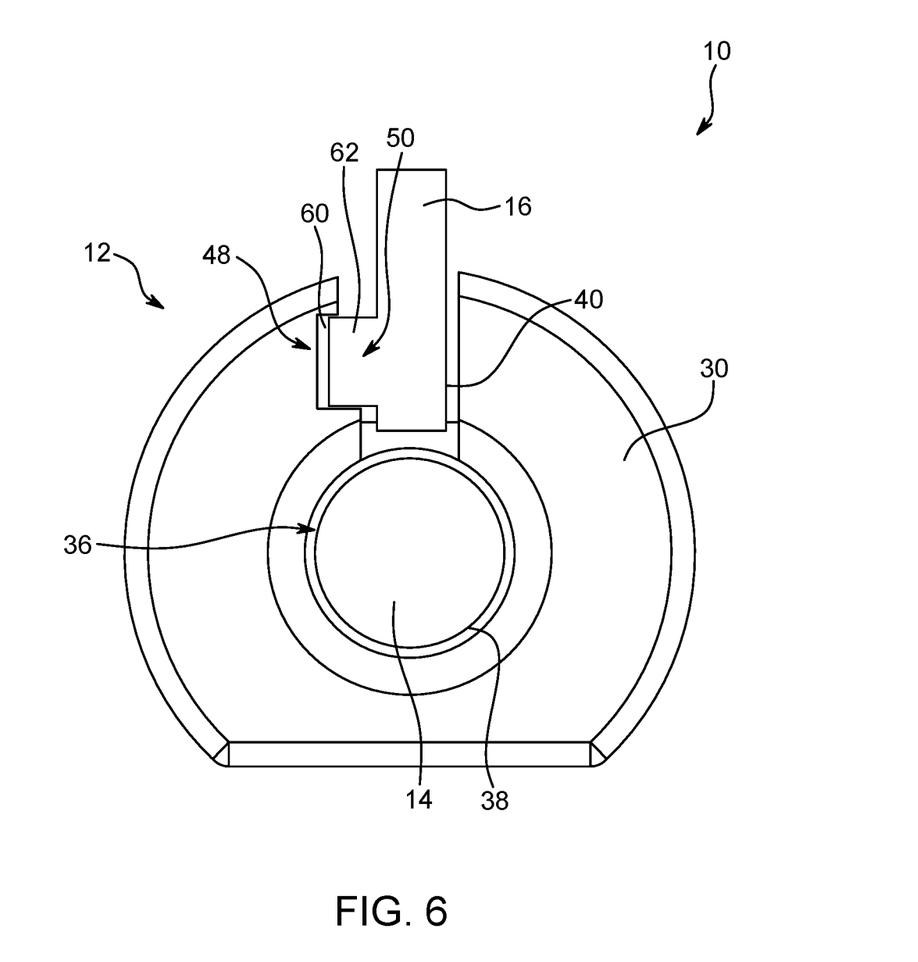
FIG. 6 is an axial view of the cannula and implements of FIG. 1 including an alternative mating feature.

FIG. 6 illustrates an alternative embodiment of the mating features 48, 50. In this embodiment, the base member 30 includes a groove 60 formed therein. The second surgical implement 16 includes a corresponding protuberance 62 which is formed to fit into the groove 60. The groove 60 may form contacting surfaces on three sides which contact and guide the protuberance 62 as the second surgical implement 16 slides axially with respect to the cannula 12.

It should be understood that the illustrated configurations of the mating feature 48, 50 are exemplary and that other configurations which allow for guided sliding of the second surgical implement 16 relative to the cannula 12 are possible. For example, other grooves and/or protuberance combinations may be implemented to guide the sliding movement.

Figure 7:
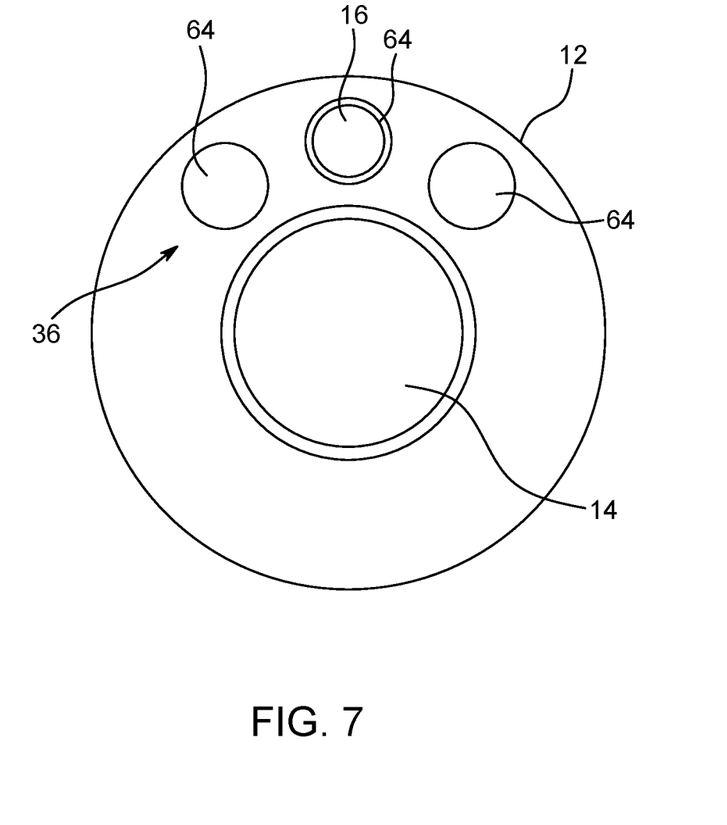
FIG. 7 is an axial view of the cannula and implements of FIG. 1, including an alternative mating feature.

FIG. 7 illustrates an alternative configuration in which the mating feature 48 formed in the base member 30 is an enclosed aperture 64. The second surgical implement 16 may include a shape which matches the enclosed aperture, thereby allowing insertion and guided movement of the second surgical implement 16. In some embodiments, the base member 30 may include a plurality of apertures 64 which selectively receive surgical implements. These additional apertures may provide additional options for positioning of the second surgical implement 16 and/or the use of multiple surgical implements at one time.

Figure 8:
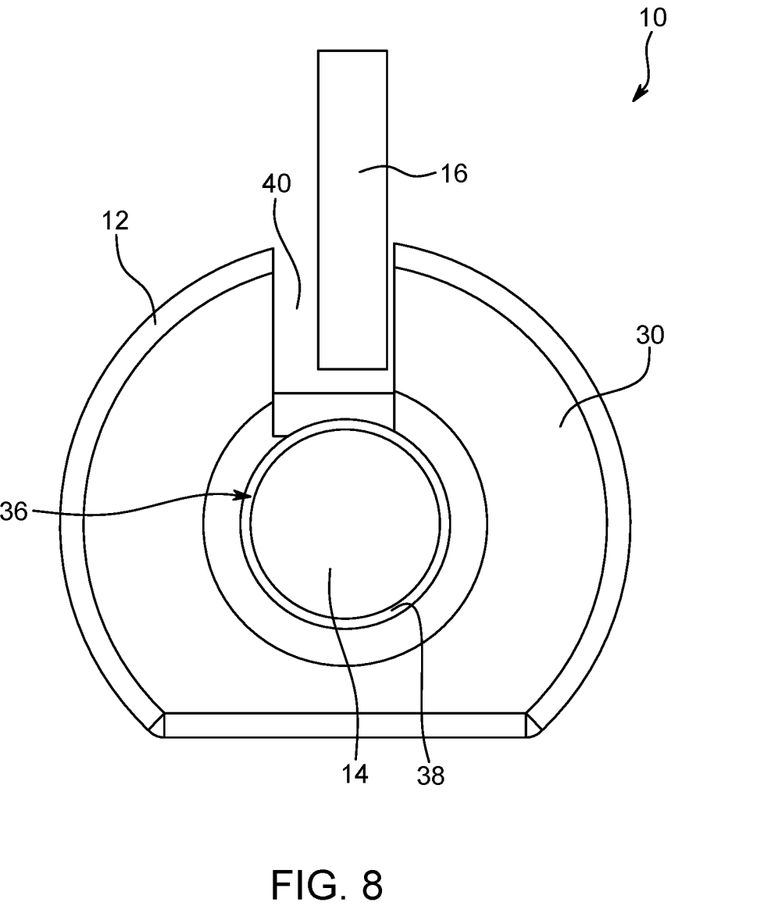
FIG. 8 is an axial view of the cannula and implements of FIG. 1 including no mating feature.

FIG. 8 illustrates another alternative embodiment of the cannula 12. In this embodiment, the combination track 36 is configured with a second section 40 which does not include a mating feature. The sliding feature 44 of the second surgical implement 16 likewise does not include a mating feature. Instead, the cannula 12 provides an open slot for receiving a portion of the second surgical implement therein.

This configuration may allow for greater maneuverability (e.g., tilting, angling, etc.) of the second surgical implement 16.

Figure 9:
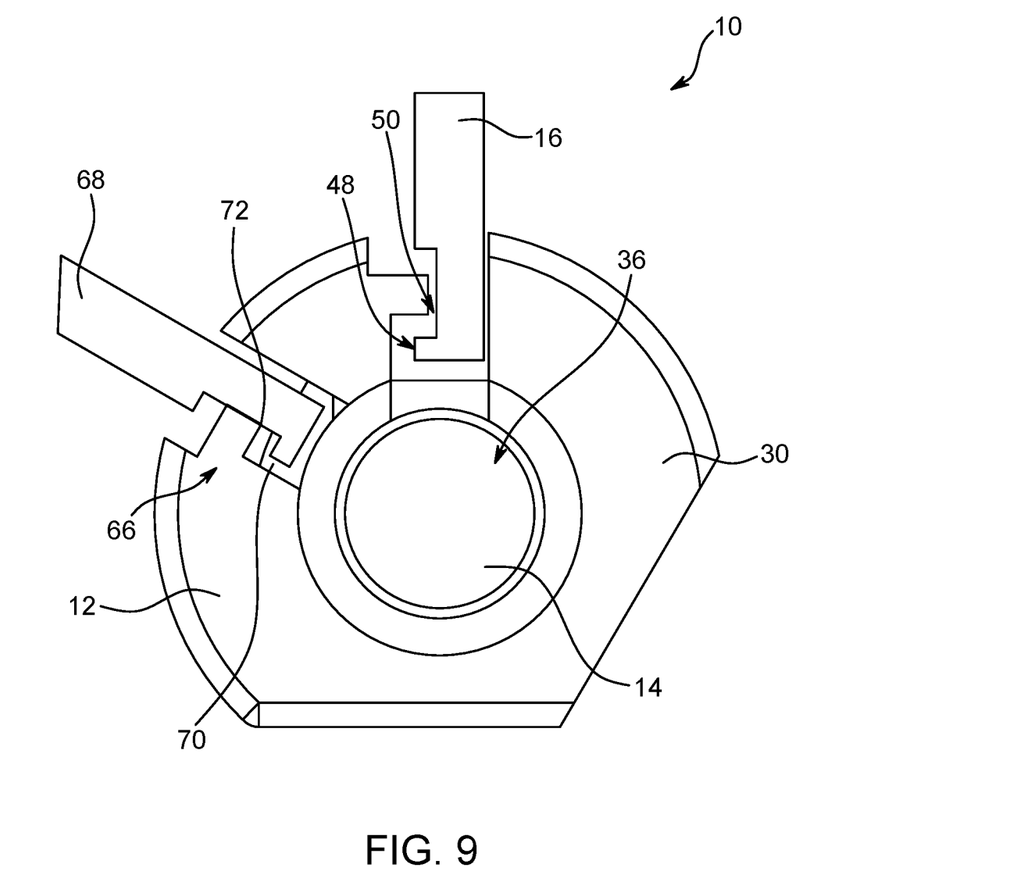
FIG. 9 is an axial view of the cannula and implements of FIG. 1, including an additional track.

FIG. 9 illustrates another alternative embodiment in which the base member 30 includes the mating feature 48 for use in combination with the mating feature 50 of the second surgical implement, as described in relation to FIGS. 4-5. In addition, however, the base member 30 includes a second track 66 which is configured to provide an alternative positioning for the second surgical implement and/or allow the simultaneous use of an additional surgical implement 68. The second track 66 and additional surgical implement 68 may include mating features 70, 72 which allow for guided sliding of the additional surgical implement 68. In at least some embodiments, the mating features 70, 72 are configured in the same manner as the mating features 48, 50 such that both the combination track 36 and the second track 66 are configured to interchangeably receive the same surgical instrument for guiding sliding movement.

Figure 10:
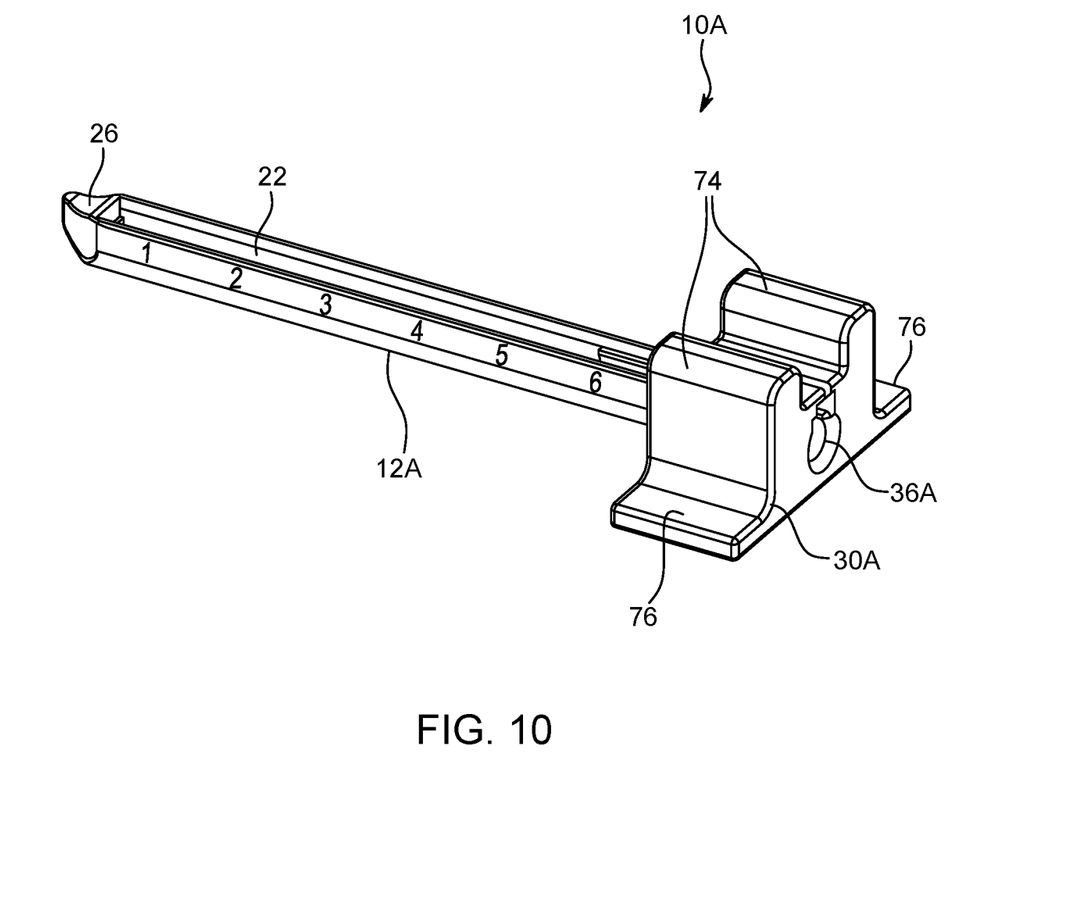
FIG. 10 is a perspective view of a cannula according to an alternative embodiment.
Figure 11:
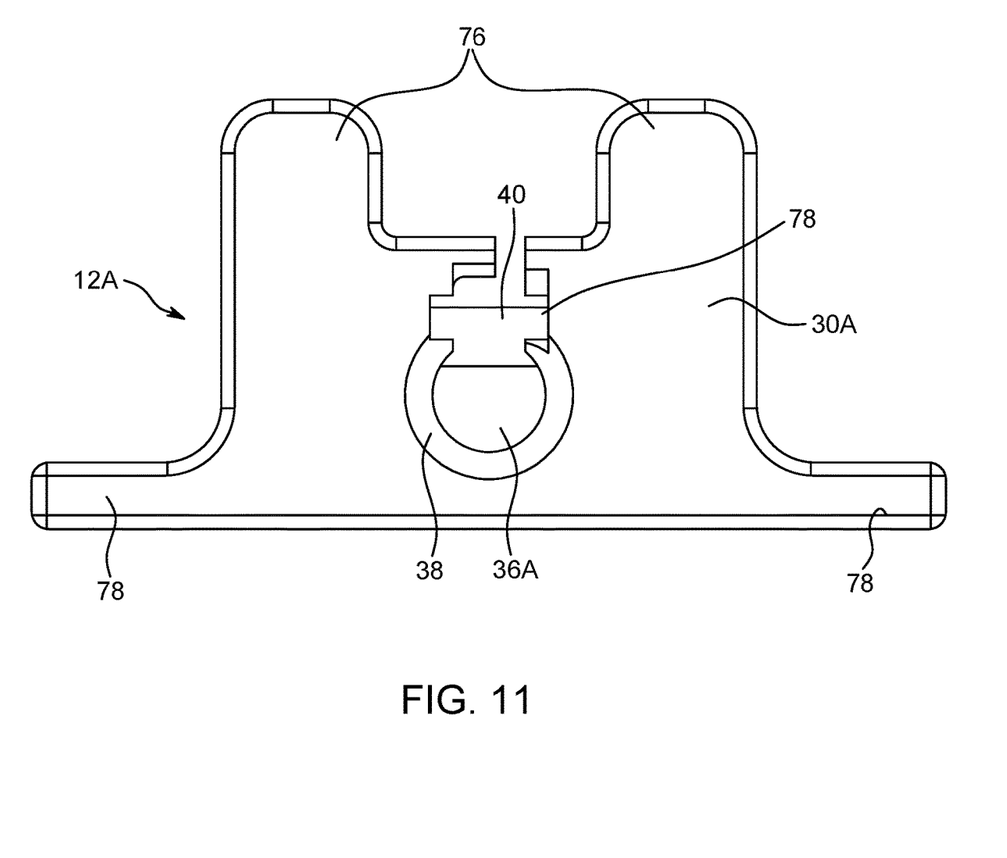
FIG. 11 is an axial view of the cannula of FIG. 10.
Figure 12:
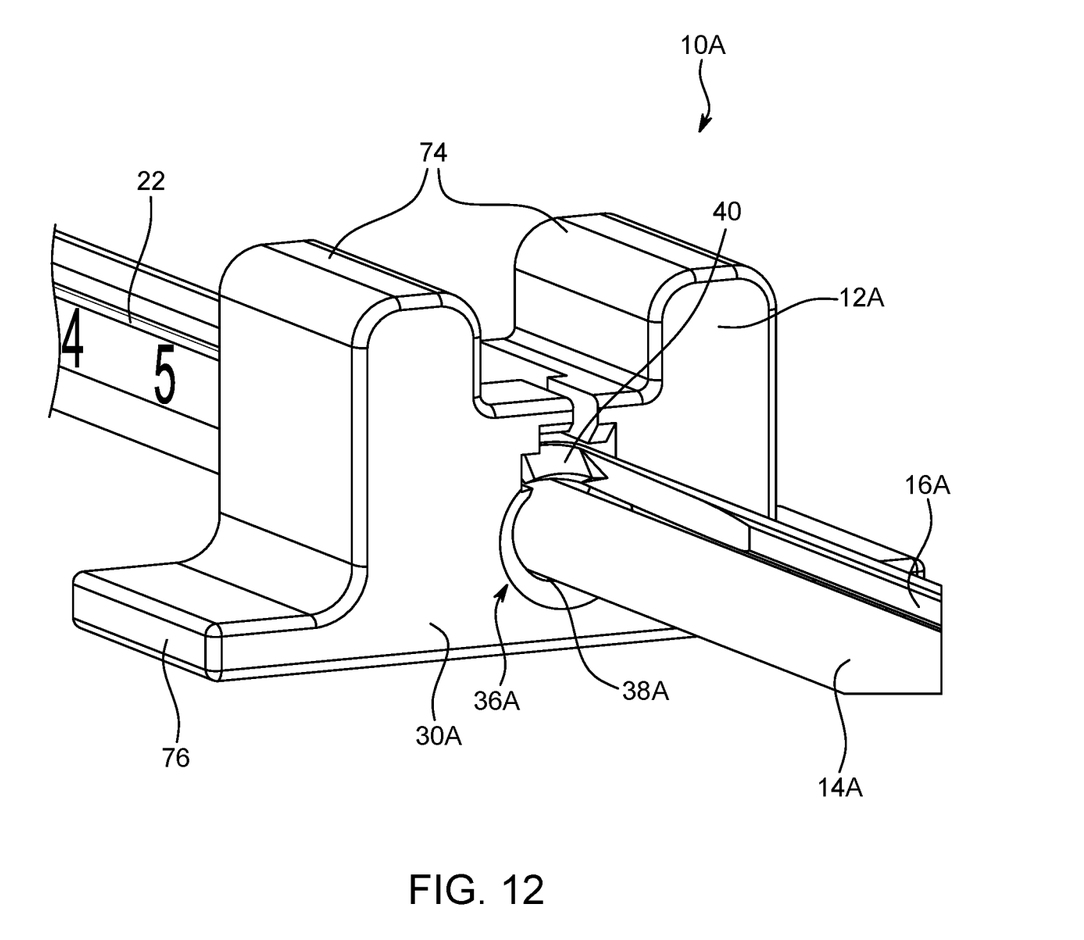
FIG. 12 is a perspective view of the cannula of FIG. 10 in combination with exemplary instruments.

FIGS. 10-12 illustrate another embodiment of the surgical device 10A, consistent with disclosed embodiments. The surgical device 10A preferably includes the herein-described features of the surgical device 10. In addition, the surgical device 10A may include some additional or alternative features. For example, the surgical device 10A may include a cannula 12A having a base member 30A at the proximal end 18 thereof. The base member 30A preferably defines a combination track 36A for receiving first and second surgical implements 14A and 16A much in the same manner as described in relation to the embodiments of surgical device 10.

In addition, the base member 30A preferably includes hubs 74 formed on opposing sides of the combination track 36A. The hubs 74 allow a person to grip the cannula 12A more easily during use. The base member 30A further includes a pair of wings 76 which extend in a direction perpendicular to the axial direction and provide a flat surface at a lower portion of the base member 30A. This flat surface rests on the patient's body, helping to stabilize the cannula 12A during use.

The combination track 36A includes a first section 38A formed as an opening into a bore 22A for receiving the first surgical implement 14A. The combination track 36A further includes a second section 40A formed as an opening into an adjacent to the bore 22A for receiving the second surgical implement 16A. The second section 40A and second surgical implement 16 include mating features 48A, 50A, respectively, which allow for guided sliding of the second surgical implement 16A.

As best shown in FIGS. 11-12, the base member 30A may also be configured such that the combination track 36A further defines, in addition to the first section 38A and the second section 40A, an accessory section 78. The accessory section 78 is configured as an additional opening which allow for greater manipulation of the second surgical implement 16A.

In one example, the accessory section 78 is configured to allow for rotation of a cutting implement as the second surgical implement 16A. In this embodiment, the second surgical implement 16A includes a cutting edge 80. The second surgical instrument 16A can be inserted into the combination track 36A in a first orientation (e.g., with the cutting edge 80 horizontally disposed). After the second surgical instrument 16A is fully inserted into the combination track 36A, the second surgical instrument 16A may be rotated to move the cutting blade into a better positioned to cut target tissue. For example, with the cutting edge 80 rotated 90 degrees from the position in which it was inserted, the cutting edge 80 may easily engage with soft tissue as the second surgical instrument 16A is pulled backward out of the cannula 12A. The space provided by the accessory section 78 allows for such rotation while still allowing the base member 30A to guide movement into and out of the cannula 12A.

The disclosed embodiments provide a surgical device which may be used in a surgical procedure. The procedure may be, for example, a soft tissue release, such as an endoscopic carpal ligament release surgery, commonly referred to as an endoscopic carpal tunnel release. Other examples include, without limitation, an endoscopic cubital tunnel release, endoscopic gastrocnemius release, endoscopic plantar fascia release, and the like.

These procedures generally include the insertion of a disclosed cannula 12 into the patient, with the distal end 20 being positioned near a target tissue. The support surface 34 provides a buffer for the bore 22, helping to separate soft tissue and inhibiting the soft tissue structures from blocking a path formed by the bore 22. A camera device is inserted into a first section 38 of the combination track 36 as a first surgical implement 14. The camera device slides through a bore 22 until it reaches the distal end 20 and provides a visualization of the target tissue. A tissue manipulation device, as a second surgical implement 16, is then inserted into a second section 40 of the combination track 36 and is guided by the corresponding surfaces of a base member 30 forming the combination track 36. The guided movement of the second surgical implement 16 allows for controlled use of an acting feature 42 of the second surgical implement 16, such as to cut, excise, or modify the target tissue. The second section 40 and second surgical implement 16 may include mating features 48, 50 which help to guide the movement. The mating features 48, 50 may take any of different configurations which help to control the sliding movement. Moreover, the mating features 48, 50 may be configured such that a variety of different surgical implements may be used in combination with the same cannula 12.

The advantages of the presently disclosed embodiments include, without limitation, providing a more accurate and repeatedly consistent method of modifying soft tissue structures. The disclosed embodiments prescribe a predefined motion of a tissue manipulation device, which helps to ensure the appropriate soft tissue structure is manipulated by the appropriate amount, and helps to prevent unwanted manipulation of adjacent soft tissue structures. The disclosed embodiments prevent excessive or inadvertent motion of a tissue manipulation device by guiding movement thereof. The disclosed embodiments also allow independent motion of an instrument and a camera device during the surgical procedure, while being in close proximity to each other. The disclosed surgical device facilitates simplified surgical steps and provides consistency as multiple types of instruments may be passed through the cannula.

Having thus described the presently preferred embodiments in detail, it is to be appreciated and will be apparent to those skilled in the art that many physical changes, only a few of which are exemplified in the detailed description of the invention, could be made without altering the inventive concepts and principles embodied therein. It is also to be appreciated that numerous embodiments incorporating only part of the preferred embodiment are possible which do not alter, with respect to those parts, the inventive concepts and principles embodied therein. The present embodiments and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

What is claimed is:

1. A cannula for use as part of a surgical device, comprising:
   a base member at a proximal terminal end of the cannula;
   a sidewall connected to the base member and extending in an axial direction from the proximal terminal end to a distal terminal end; and
   a bore extending in the axial direction defined by the base member and the sidewall, the sidewall further defining an opening into the bore between axially-extending edges of the sidewall;
   wherein the base member includes a combination track including a first section and a second section, the first section being a circular opening through the base member into the bore and the second section located above the first section and being an opening into an action area outside of the bore and radially between the edges of the sidewall, the first section and the second section being interconnected to form a single opening of the combination track, the second section of the combination track extending between axial end faces of the base member and defining an opening between a radially inner edge of a wall of the base member and a radially outer edge of the wall of the base member,
   wherein the combination track is configured to slidably receive a camera device through the first section and into the bore and slidably receive a tissue manipulation device through the second section and into the action area such that the camera device is positioned below the tissue manipulation device, the camera device and the tissue manipulation device are configured to be inserted into the cannula independent from each other, and the camera device and the tissue manipulation device are configured to be moved independently from each other within the cannula, and
   the base member includes a first mating feature having at least one protuberance configured to engage with a second mating feature on the tissue manipulation device such that the tissue manipulation device is freely slidable within the base member, the at least one protuberance being axially defined within the base member and positioned away from the action area.

2. The cannula of claim 1, wherein the tissue manipulation device includes a surgical blade configured to cut soft tissue.

3. The cannula of claim 1, wherein the second mating feature includes a groove extending in the axial direction.

4. The cannula of claim 1, further including a support surface at the distal terminal end configured to support soft tissue of a patient.

5. The cannula of claim 4, wherein the support surface is flat and extends in a direction perpendicular to the axial direction.

6. The cannula of claim 1, wherein the opening of second section is enclosed by the base member.

7. The cannula of claim 6, wherein the base member includes a plurality of radially offset openings for receiving the second surgical implement.

8. The cannula of claim 1, wherein the base member further includes a second track for receiving another surgical implement.

9. The cannula of claim 8, wherein the second section of the combination track includes a mating feature for guiding the second surgical implement and the second track includes a mating feature for guiding the another surgical implement.

10. The cannula of claim 9, wherein the mating features include the same configuration such that the second track is configured to guide the second surgical implement.

11. The cannula of claim 1, wherein the camera device and the tissue manipulation device are configured to be independently stacked adjacent to each other within the base member.

12. A surgical device, comprising:
    a camera device;
    a tissue manipulation device including an acting feature and a sliding feature, the tissue manipulation device being separate and independent from the camera device; and
    a cannula comprising:
      a base member at a proximal terminal end;
      a sidewall connected to the base member and extending in an axial direction from the proximal terminal end to a distal terminal end; and
      a bore extending in the axial direction defined by the base member and the sidewall, the sidewall further defining an opening into the bore between axially-extending edges of the sidewall;
      wherein the base member includes a combination track including a first section and a second section, the first section being a circular opening through the base member into the bore and the second section located above the bore and being an opening into an action area outside of the bore and radially between the edges of the sidewall, the first section and the second section being interconnected to form a single opening of the combination track, the second section of the combination track extending between axial end faces of the base member and defining an opening between a radially inner edge of a wall of the base member and a radially outer edge of the wall of the base member,
      wherein the combination track slidably receives the camera device through the first section and into the bore and slidably receives the tissue manipulation device through the second section and into the action area via the sliding feature such that the camera device is positioned below the tissue manipulation device and the camera device and the tissue manipulation device are independently moveable relative to each other within the cannula, and
      the base member includes a first mating feature having at least one protuberance configured to engage with a second mating feature on the tissue manipulation device such that the tissue manipulation device is freely slidable within the base member, the at least one protuberance being axially defined within the base member and positioned away from the action area.

13. The surgical device of claim 12, wherein the tissue manipulation device is a cutting tool with the acting feature being a blade.

14. The surgical device of claim 13, wherein the combination track further includes an accessory section configured to permit rotation of the cutting tool when the cutting tool is in the action area.

15. The surgical device of claim 12, wherein the first mating feature is positioned in the second section and the tissue manipulation device includes a corresponding mating feature in the sliding feature.

16. The surgical device of claim 15, wherein the corresponding mating feature includes a groove configured to engage the protuberance.

17. The surgical device of claim 12, wherein the camera device and the tissue manipulation device are configured to be independently inserted within the cannula.

18. The surgical device of claim 12, wherein the camera device and the tissue manipulation device are configured to be independently stacked adjacent to each other within the base member.

* * * * *